(12) United States Patent
Govari et al.

(10) Patent No.: US 10,390,870 B2
(45) Date of Patent: Aug. 27, 2019

(54) UNCALIBRATED THERMOCOUPLE SYSTEM

(71) Applicant: BIOSENSE WEBSTER (ISRAEL) LTD., Yokneam (IL)

(72) Inventors: Assaf Govari, Haifa (IL); Yaron Ephrath, Karkur (IL); Meir Bar-Tal, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 0 days.

(21) Appl. No.: 16/158,896

(22) Filed: Oct. 12, 2018

(65) Prior Publication Data

US 2019/0076178 A1 Mar. 14, 2019

Related U.S. Application Data

(63) Continuation of application No. 15/091,860, filed on Apr. 6, 2016, now Pat. No. 10,098,684.

(51) Int. Cl.
*G01K 7/00* (2006.01)
*H03M 1/00* (2006.01)
(Continued)

(52) U.S. Cl.
CPC .............. *A61B 18/00* (2013.01); *A61B 5/062* (2013.01); *A61B 18/1492* (2013.01); *G01K 7/14* (2013.01);
(Continued)

(58) Field of Classification Search
CPC ..... A61B 18/00; A61B 5/062; A61B 18/1492; A61B 2018/00351; A61B 2018/00577;
(Continued)

(56) References Cited

U.S. PATENT DOCUMENTS 5,821,889 A 10/1998 Miller
6,402,742 B1 6/2002 Blewett et al.
(Continued)

FOREIGN PATENT DOCUMENTS

EP 2 485 395 A1 8/2012

OTHER PUBLICATIONS

European Search Report dated Sep. 15, 2017 in corresponding European Patent Application No. 17164965.0.

*Primary Examiner* — Kenneth B Wells
(74) *Attorney, Agent, or Firm* — Lewis Roca Rothgerber Christie LLP

(57) ABSTRACT

Apparatus, including a multiplexer, having a first output and multiple first inputs receiving analog input signals and an analog feedback signal and cycling through and selecting the signals for transfer in sequential signal groupings to the first output. The apparatus also includes an amplification circuit, having a second output and a second input connected to the multiplexer first output, that amplifies signals corresponding to the analog input signals with a selected gain so as to generate respective amplified analog signals at the second output. Circuitry selects a characteristic of the respective amplified analog signals from an initial signal grouping, feeds the characteristic back for input to the multiplexer as the analog feedback signal, selects a subsequent characteristic of the respective amplified analog signals from a subsequent signal grouping, and adjusts the amplification circuit gain so that the analog feedback signal and the subsequent characteristic have the same amplitude.

20 Claims, 5 Drawing Sheets

(51) Int. Cl.
*A61B 18/00* (2006.01)
*A61B 5/06* (2006.01)
*A61B 18/14* (2006.01)
*G01K 7/14* (2006.01)
*H03M 1/12* (2006.01)
*H03M 1/08* (2006.01)
*H03M 1/18* (2006.01)

(52) U.S. Cl.
CPC . *H03M 1/1225* (2013.01); *A61B 2018/00351* (2013.01); *A61B 2018/00577* (2013.01); *A61B 2018/00642* (2013.01); *A61B 2018/00821* (2013.01); *H03M 1/08* (2013.01); *H03M 1/183* (2013.01)

(58) Field of Classification Search
CPC ........... A61B 2018/00642; G01K 7/14; H03M 1/1225
See application file for complete search history.

(56) References Cited

U.S. PATENT DOCUMENTS

| | | |
|---|---|---|
| 6,414,619 B1 | 7/2002 | Swanson |
| 6,462,505 B1 | 10/2002 | Spingler |
| 6,999,011 B2 | 2/2006 | Case et al. |
| 7,313,706 B2 | 12/2007 | Williams et al. |
| 7,344,533 B2 | 3/2008 | Pearson et al. |
| 7,461,554 B2 | 12/2008 | Thomas et al. |
| 7,545,200 B2 | 6/2009 | Kreda |
| 8,437,832 B2 | 5/2013 | Govari et al. |
| 8,644,523 B2 | 2/2014 | Clemow |
| 9,226,791 B2 | 1/2016 | McCarthy et al. |
| 10,098,684 B2 * | 10/2018 | Govari ................... A61B 5/062 |
| 2011/0130648 A1 | 6/2011 | Beeckler et al. |
| 2011/0257563 A1 | 10/2011 | Thapliyal et al. |
| 2014/0171821 A1 | 6/2014 | Govari et al. |

* cited by examiner

UNCALIBRATED THERMOCOUPLE SYSTEM

CROSS-REFERENCE TO RELATED APPLICATION(S)

This application is a continuation of U.S. application Ser. No. 15/091,860 filed Apr. 6, 2016, now U.S. Pat. No. 10,098,684 the entire content of which is incorporated herein by reference.

FIELD OF THE INVENTION

The present invention relates generally to circuitry, and specifically to circuitry for handling thermocouple signals.

BACKGROUND OF THE INVENTION

Thermocouple signals are typically in the millivolt or even microvolt range, and thermocouples inherently usually have a relatively high impedance. Both factors, the low signal levels and the high source impedance, lead to signals from the thermocouples being very susceptible to noise. In addition, particularly in a medical scenario such as an ablation procedure, where thermocouples may be used for critical measurements on patients, it is important that noise from thermocouples is reduced and that the signals derived from the thermocouples give true temperature readings. Methods for compensating or reducing noise levels from thermocouples, and for ensuring that the signals are valid, are known in the art.

For example, U.S. Pat. No. 6,402,742, to Blewett, et al., whose disclosure is incorporated herein by reference, describes a temperature measuring circuit which is coupled to the prostate and urethral thermocouples. The disclosure also describes a controller which operates from AC line voltage that is filtered to reduce noise.

U.S. Pat. No. 8,644,523, to Clemow, whose disclosure is incorporated herein by reference, describes a digital circuit arrangement for an ambient noise-reduction system. The arrangement converts analog signals into N-bit digital signals at a sample rate and then subjects the converted signals to digital filtering.

U.S. Pat. No. 9,226,791, to McCarthy et al., whose disclosure is incorporated herein by reference, describes an interface module which may include an input/output (I/O) port that receives digital thermocouple signals from an integrated catheter tip. The digital signals are provided by an analog-to-digital converter.

Documents incorporated by reference in the present patent application are to be considered an integral part of the application except that, to the extent that any terms are defined in these incorporated documents in a manner that conflicts with definitions made explicitly or implicitly in the present specification, only the definitions in the present specification should be considered.

SUMMARY OF THE INVENTION

An embodiment of the present invention provides apparatus, including:

a multiplexer, having a first output and multiple first inputs configured to receive a plurality of analog input signals and an analog feedback signal and configured to cycle through and select the signals in alternation for transfer in sequential signal groupings to the first output;

an amplification circuit having a second output and a second input connected to the first output of the multiplexer and configured to amplify signals in the signal groupings corresponding to the plurality of analog input signals with a selected gain so as to generate respective amplified analog signals at the second output; and a processor, having a third input connected to the second output of the amplification circuit, and having a third output coupled to one of the first inputs of the multiplexer, and including control circuitry configured to select a predetermined characteristic of the respective amplified analog signals from an initial signal grouping, to feed the predetermined characteristic back via the third output for input to the multiplexer as the analog feedback signal, to select a subsequent predetermined characteristic of the respective amplified analog signals from a subsequent signal grouping, and to adjust the gain of the amplification circuit so that the analog feedback signal and the subsequent predetermined characteristic have the same amplitude.

In an embodiment the amplification circuit has an overall gain of unity.

In an alternative embodiment the amplification circuit consists of an amplifier having a gain greater than unity and coupled to receive and amplify the sequential signal groupings. The amplification circuit may include an analog-to-digital converter coupled to receive and digitize the amplified sequential signal groupings. The control circuitry may be configured to select the predetermined characteristic of the respective amplified analog signals by analysis of the digitized amplified sequential signal groupings.

In a further alternative embodiment the amplification circuit includes an amplifier having a gain less than unity and coupled to receive the amplified signals in the signal groupings corresponding to the plurality of analog input signals.

In a yet further alternative embodiment the apparatus includes a catheter having a plurality of thermocouples respectively generating the plurality of analog input signals.

In a disclosed embodiment the predetermined characteristic consists of one of a maximum, a mean, and a minimum of the respective amplified analog signals.

There is further provided a method, including:

configuring a multiplexer, having a first output and multiple first inputs to receive a plurality of analog input signals and an analog feedback signal and to cycle through and select the signals in alternation for transfer in sequential signal groupings to the first output;

configuring an amplification circuit having a second output and a second input connected to the first output of the multiplexer to amplify signals in the signal groupings corresponding to the plurality of analog input signals with a selected gain so as to generate respective amplified analog signals at the second output;

selecting a predetermined characteristic of the respective amplified analog signals from an initial signal grouping;

feeding the predetermined characteristic back for input to the multiplexer as the analog feedback signal;

selecting a subsequent predetermined characteristic of the respective amplified analog signals from a subsequent signal grouping; and adjusting the gain of the amplification circuit so that the analog feedback signal and the subsequent predetermined characteristic have the same amplitude.

The present disclosure will be more fully understood from the following detailed description of the embodiments thereof, taken together with the drawings, in which:

DETAILED DESCRIPTION OF EMBODIMENTS

Overview

Figure 1:
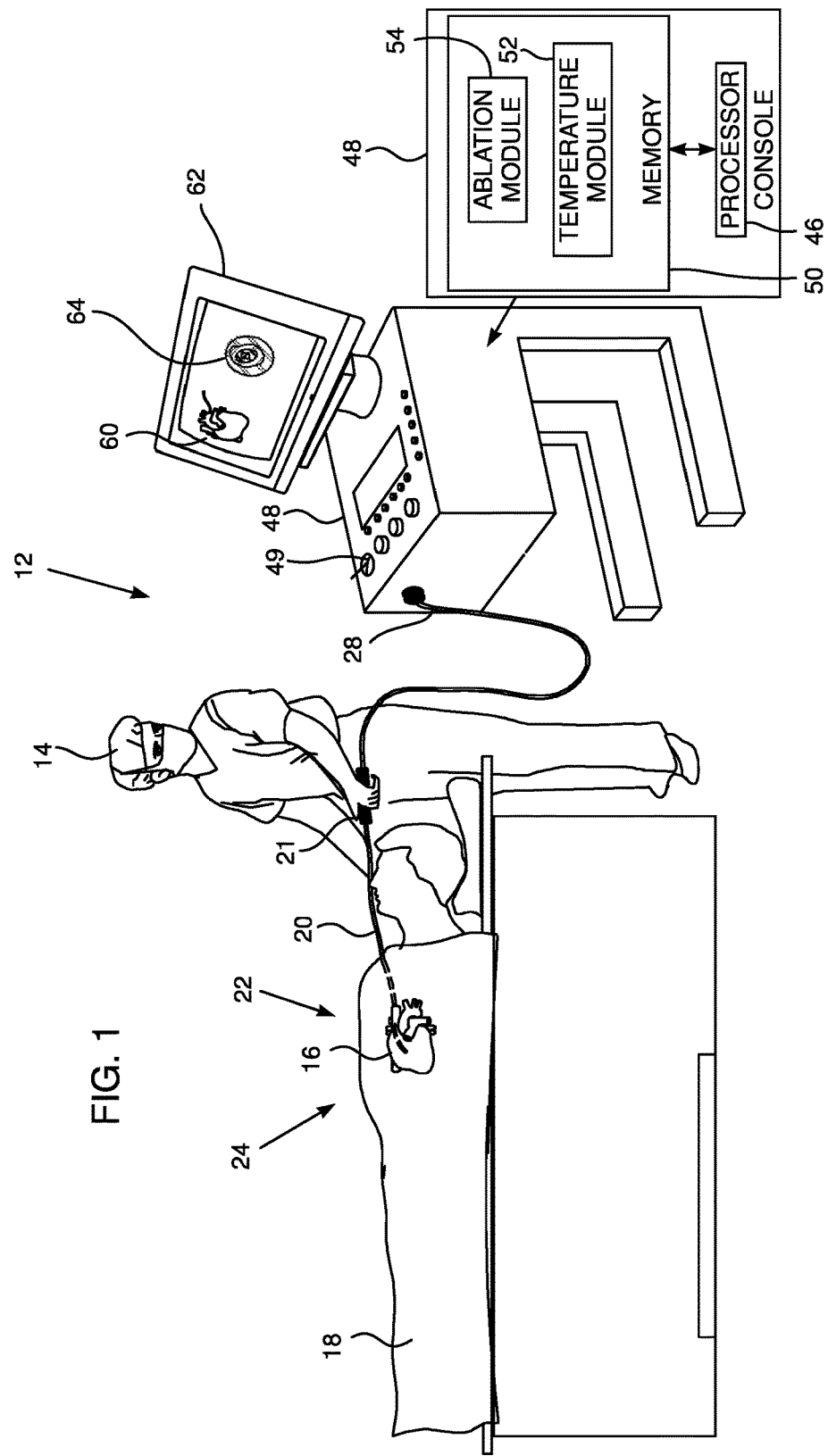
FIG. 1 is a schematic illustration of an invasive medical procedure, according to an embodiment of the present invention.

Typically, signals from thermocouples may be inaccurate and/or unstable, because of, for example, noise induced in the signal lines and temperature variations along the lines. In the case of groups of thermocouples which may be in close physical proximity and which are typically at similar temperatures, the inaccuracy and/or instability leads to mismatching between the signals and consequent misleading temperature readings.

Embodiments of the present invention overcome these problems by processing all the signals, typically from a group of thermocouples, through the same circuit, so ensuring that all output signals are matched.

The circuit comprises a multiplexer which receives a plurality of analog input signals and an analog feedback signal, and which transfers the signals in a signal grouping to an amplification circuit. The amplification circuit amplifies signals in the signal grouping corresponding to the plurality of analog input signals with a selected gain so as to generate respective amplified analog signals.

A processor is connected to receive the amplified analog signals. In addition the processor comprises control circuitry which is configured to select a maximum of the amplified analog signals from an initial signal grouping and to feed the maximum back to the multiplexer as the analog feedback signal. The control circuitry is further configured to select a maximum of the amplified analog signals from a subsequent signal grouping, and to adjust the gain of the amplification circuit so that the analog feedback signal and the subsequent maximum have the same amplitude.

System Description

In the following description, like elements in the drawings are identified by like numerals, and the like elements are differentiated as necessary by appending a letter to the identifying numeral.

FIG. 1 is a schematic illustration of an invasive medical procedure using apparatus 12, according to an embodiment of the present invention. The procedure is performed by a medical professional 14, and, by way of example, the procedure in the description hereinbelow is assumed to comprise ablation of a portion of a myocardium 16 of the heart of a human patient 18. However, it will be understood that embodiments of the present invention are not just applicable to this specific procedure, and may include substantially any procedure on biological tissue or on non-biological material.

In order to perform the ablation, professional 14 inserts a probe 20 into a lumen of the patient, using a probe handle 21, so that a distal end 22 of the probe enters the heart of the patient. Distal end 22 comprises electrodes 24 mounted on the outside of the distal end, the electrodes contacting respective locations of the myocardium. Probe 20 has a proximal end 28. Distal end 22 of the probe is described in more detail below with reference to FIGS. 2A, 2B and 2C.

Apparatus 12 is controlled by a system processor 46, which is located in an operating console 48 of the apparatus. Console 48 comprises controls 49 which are used by professional 14 to communicate with the processor. During the procedure, processor 46 typically tracks a location and an orientation of distal end 22 of the probe, using any method known in the art. For example, processor 46 may use a magnetic tracking method, wherein magnetic transmitters external to patient 18 generate signals in coils positioned in the distal end. The Carto® system produced by Biosense Webster, of Diamond Bar, Calif., uses such a tracking method.

The software for processor 46 may be downloaded to the processor in electronic form, over a network, for example. Alternatively or additionally, the software may be provided on non-transitory tangible media, such as optical, magnetic, or electronic storage media. The track of distal end 22 is typically displayed on a three-dimensional representation 60 of the heart of patient 18 on a screen 62.

In order to operate apparatus 12, processor 46 communicates with a memory 50, which has a number of modules used by the processor to operate the apparatus. Thus, memory 50 comprises a temperature module 52 and an ablation module 54, the functions of which are described below. Memory 50 typically comprises other modules, such as a force module for measuring the force on end 22, a tracking module for operating the tracking method used by processor 46, and an irrigation module allowing the processor to control irrigation provided for distal end 22. For simplicity, such other modules, which may comprise hardware as well as software elements, are not illustrated in FIG. 1.

Processor 46 typically uses results of measurements of temperature acquired by module 52 to display on screen 62 a temperature distribution map 64.

Figure 2A:
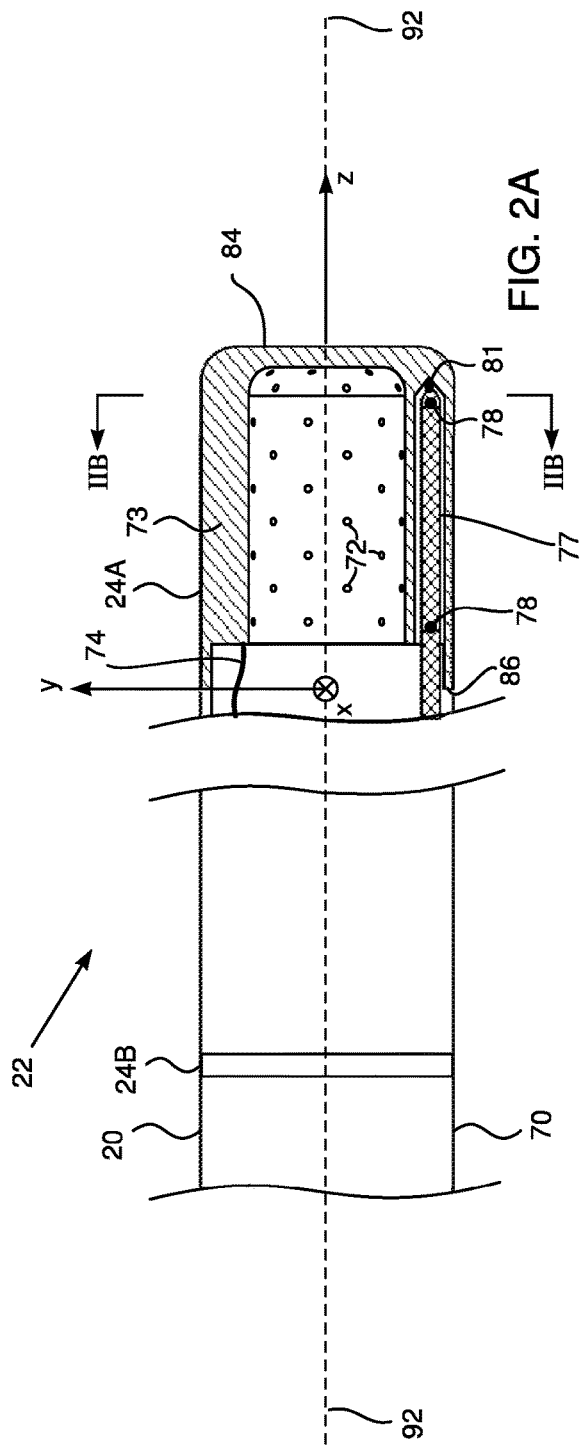
FIGS. 2A, 2B, and 2C schematically illustrate a distal end of a probe, according to an embodiment of the present invention.
Figure 2C:
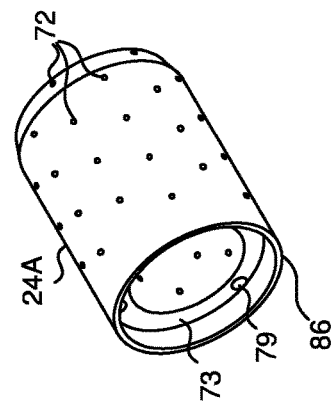
Figure 2B:
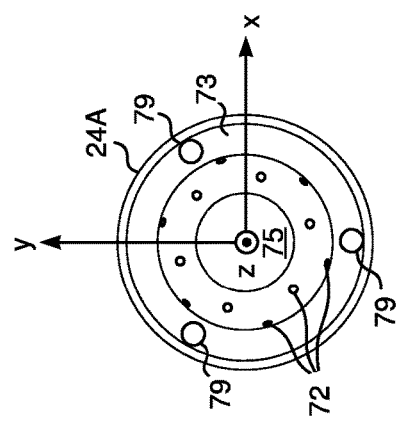

FIGS. 2A, 2B, and 2C schematically illustrate distal end 22 of probe 20, according to an embodiment of the present invention. FIG. 2A is a sectional view along the length of the probe, FIG. 2B is a cross-sectional view along a cut IIB-IIB that is marked in FIG. 2A, and FIG. 2C is a perspective view of a section of the distal end. An insertion tube 70 extends along the length of the probe and is connected at the termination of its distal end to a conductive cap electrode 24A, which is assumed herein to be used for ablation. FIG. 2C is a schematic perspective view of cap electrode 24A. Cap electrode 24A has an approximately plane conducting surface 84 at its distal end and a substantially circular edge 86 at its proximal end. Conductive cap electrode 24A is herein also termed the ablation electrode. Proximal to ablation electrode 24A there are typically other electrodes such as an electrode 24B. Typically, insertion tube 70 comprises a flexible, biocompatible polymer, while electrodes 24A, 24B comprise a biocompatible metal, such as gold or platinum, for example. Ablation electrode 24A is typically perforated by an array of irrigation apertures 72.

An electrical conductor 74 conveys radio-frequency (RF) electrical energy from ablation module 54 (FIG. 1), through insertion tube 70, to electrode 24A, and thus energizes the electrode to ablate myocardial tissue with which the electrode is in contact. Module 54 controls the level of RF power dissipated via electrode 24A. During the ablation procedure, cooling fluid flowing out through apertures 72 may irrigate the tissue under treatment.

Temperature sensors 78, comprising thermocouples which are typically copper-constantan thermocouples, and also referred to herein as thermocouples 78, are mounted within conductive cap electrode 24A at locations that are arrayed around the distal tip of the probe, both axially and circumferentially. In this example, cap 24A contains six sensors, with one group of three sensors in a distal location, close to the tip, and another group of three sensors in a slightly more proximal location. This distribution is shown only by way of example, however, and greater or smaller numbers of sensors may be mounted in any suitable locations within the cap. Thermocouples 78 are connected by leads (not shown in the diagram) running through the length of insertion tube 70 to provide temperature signals to temperature module 52.

In a disclosed embodiment cap 24A comprises a side wall 73 that is relatively thick, on the order of 0.5 mm thick, in order to provide the desired thermal insulation between temperature sensors 78 and the cooling fluid inside a central cavity 75 of the tip. The cooling fluid exits cavity 75 through apertures 72. Sensors 78 are mounted on rods 77, which are fitted into longitudinal bores 79 in side wall 73. Rods 77 may comprise a suitable plastic material, such as polyimide, and may be held in place at their distal ends by a suitable cement 81, such as epoxy. U.S. Patent Publication 2014/0171821, which is incorporated herein by reference, describes a catheter having temperature sensors mounted in a similar configuration to that described above. The arrangement described above provides an array of six sensors 78, but other arrangements, and other numbers of sensors, will be apparent to those having ordinary skill in the art, and all such arrangements and numbers are included within the scope of the present invention.

In the description herein, distal end 22 is assumed to define a set of xyz orthogonal axes, where an axis 92 of the distal end corresponds to the z axis of the set. For simplicity and by way of example, the y axis is assumed to be in the plane of the paper, the xy plane is herein assumed to correspond to the plane defined by circle 86, and the origin of the xyz axes is assumed to be the center of the circle.

Typically, distal end 22 contains other functional components, which are outside the scope of the present disclosure and are therefore omitted for the sake of simplicity. For example, the distal end of the probe may contain steering wires, as well as sensors of other types, such as a position sensor and a force sensor. Probes containing components of these kinds are described, for example, in U.S. Pat. No. 8,437,832 and U.S. Patent Publication 2011/0130648, which are incorporated herein by reference.

Figure 3:
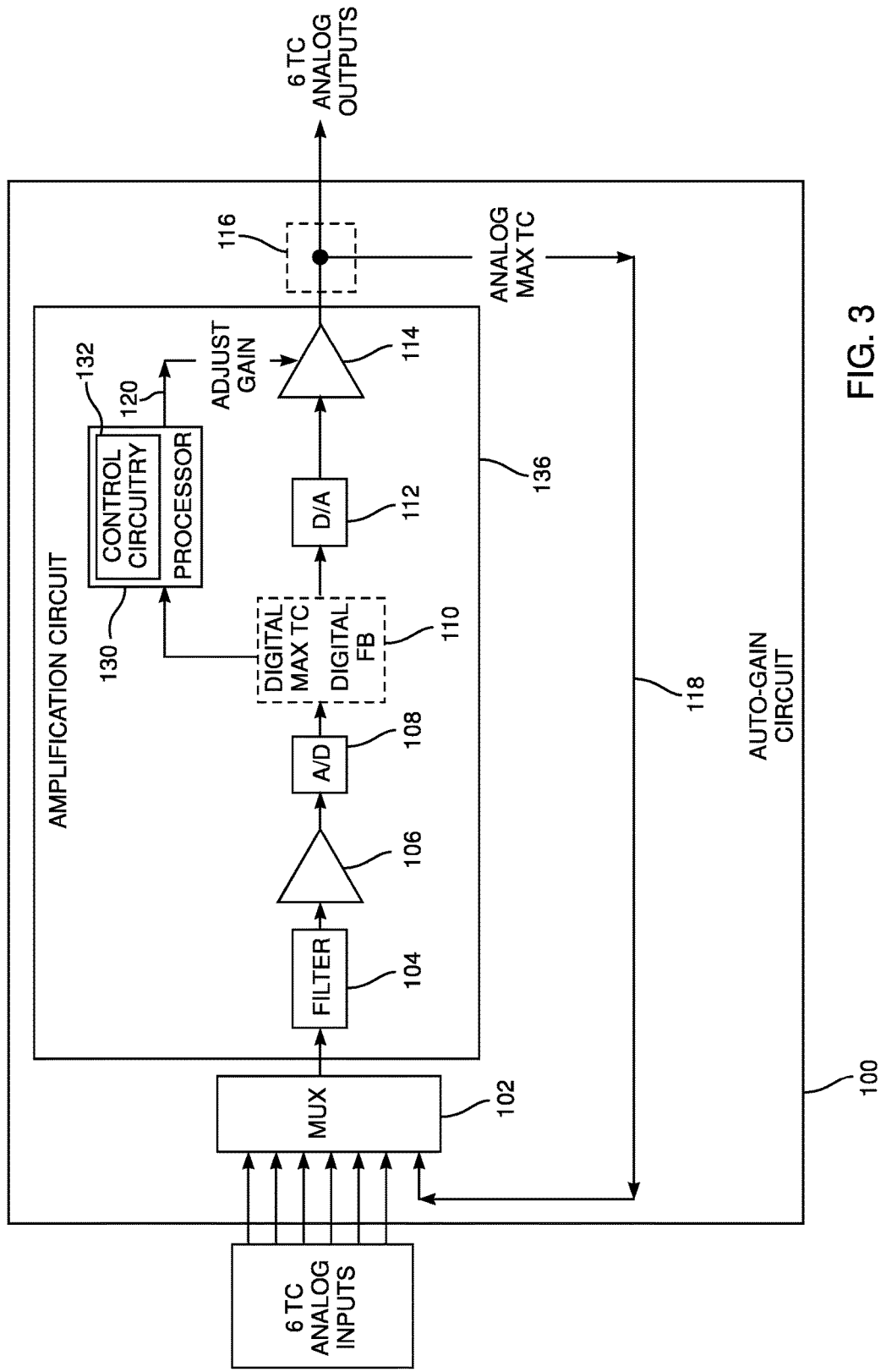
FIG. 3 is a schematic block diagram of an auto-gain circuit used for receiving signals from thermocouples, according to an embodiment of the present invention.
Figure 4:
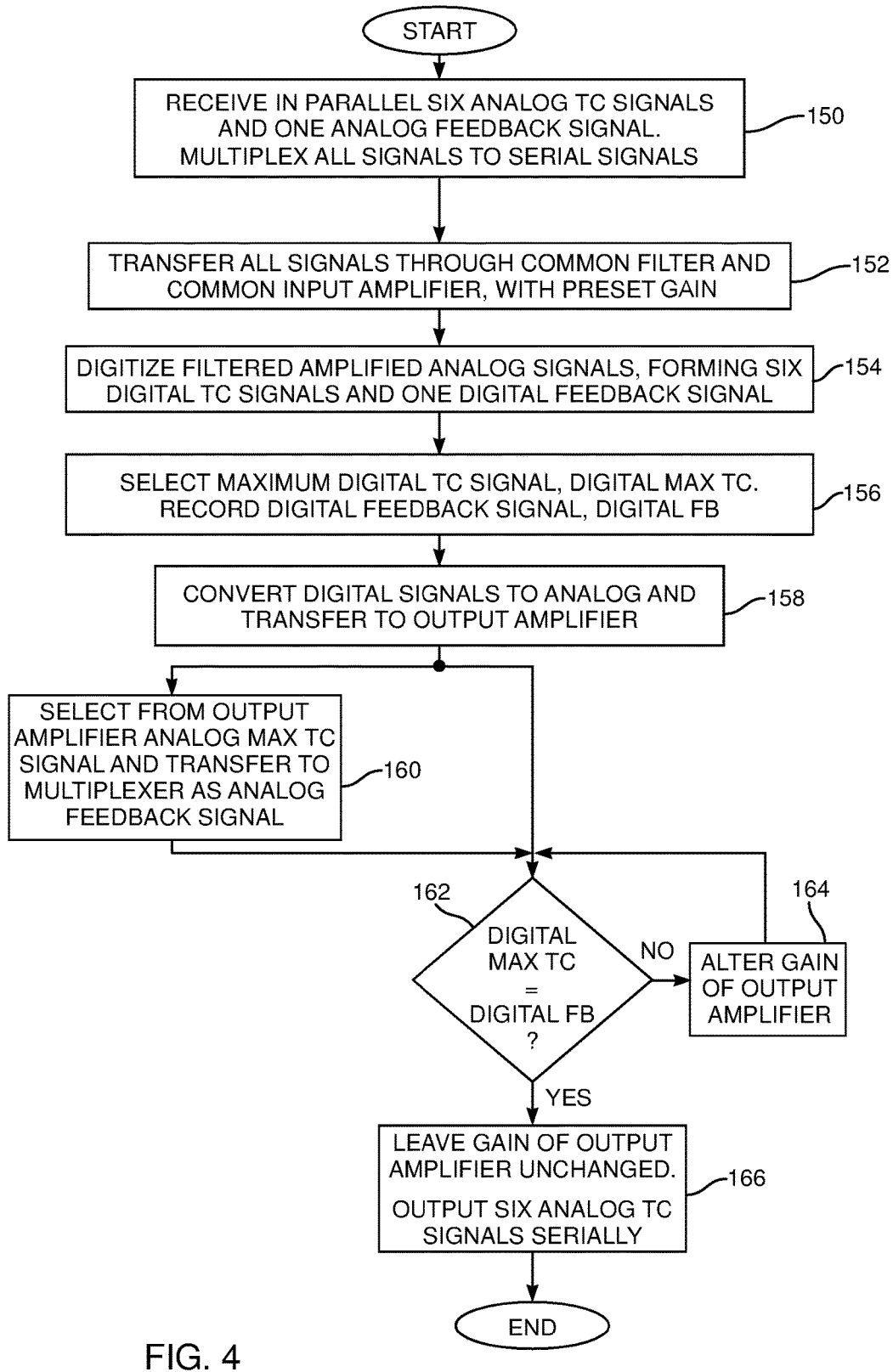
FIG. 4 is a flowchart of actions performed by the circuit of FIG. 3, according to an embodiment of the present invention.

FIG. 3 is a schematic block diagram of an auto-gain circuit 100 used for receiving the signals from thermocouples 78, and FIG. 4 is a flowchart of actions performed by the circuit, according to an embodiment of the present invention.

Typically, the signals from thermocouples 78 may be inaccurate and/or unstable, because of, for example, noise induced in the signal lines and temperature variations along the lines. Even with these effects occurring, circuit 100 selects a predetermined characteristic of the signals, and provides a feedback mechanism that ensures that a level of the characteristic is output accurately. Since the signals other than the characteristic are processed through the same circuitry as the characteristic, all output signals from the circuit are matched.

The predetermined characteristic of the signal may be any measurable characteristic of the signal, such as a maximum of the signal, a mean of the signal, or a minimum of the signal. For simplicity in the following description of the flowchart of FIG. 4 and of circuit 100, the predetermined characteristic is assumed to comprise the maximum of the signal, and those having ordinary skill in the art will be able to adapt the description, mutatis mutandis, for signal characteristics other than the maximum.

Circuit 100 is typically incorporated in temperature module 52 in console 48, although in some embodiments the circuit is incorporated into handle 21 of probe 20. In the following description, by way of example, elements of circuit 100 are assumed to be under overall control of a dedicated processor 130, incorporated into the circuit, and the processor is also assumed to have control circuitry 132, which may be implemented in hardware and/or software, to operate the circuit, so that the circuit is able to operate as a stand-alone unit. However, it will be appreciated that the elements could be controlled and operated by any processor, such as processor 46, and those having ordinary skill in the art will be able to adapt the description herein, without undue experimentation, to accommodate such a case.

While in the following description circuit 100 is assumed, for clarity, to receive inputs from six thermocouples 78 it will be understood that embodiments of the present invention may be implemented to receive inputs from more or less than six thermocouples.

As shown in an initial step 150, a multiplexer 102 receives in parallel signals from the six thermocouples 78 as six baseband analog potential signals. The multiplexer also receives a seventh baseband analog potential signal, which is a feedback signal generated by components of circuit 100. Multiplexer 102 cycles through and selects each of its 7 analog inputs in turn, and outputs the selected inputs serially as a signal grouping to a low-pass filter 104. In a disclosed embodiment, filter 104 has a cut-off frequency between 10 Hz and 50 Hz. The feedback signal is derived from a previous signal grouping that has passed through the circuit, and the production of the feedback signal is described in more detail below.

In a filtering and amplifying step 152, after traversing filter 104, the grouping of analog signals is input to an amplifier 106, which outputs its amplified signals to an analog-to-digital (A/D) converter 108. Amplifier 106 has a preset gain selected so that the output of the amplifier is within the dynamic range of A/D converter 108. Amplifier 106 typically has a gain of approximately 100.

In a digitizing step 154 A/D converter 108 generates seven digital signals, corresponding to the seven analog signals it has received from amplifier 106. The seven digital signals consist of six digital signals derived from thermocouples 78, and one digital feedback signal.

In a first analysis step 156, circuitry 132 analyzes the six digital signals from the thermocouples, and finds which of the signals has a maximum value DIGITAL MAX TC. The processor also records the value of the digital feedback signal DIGITAL FB. The analysis and recording operation is illustrated schematically in FIG. 3 by a dashed block 110.

In a conversion step 158, the digital signals from A/D converter 108, including the six digital signals corresponding to the thermocouple signals, are converted back to analog signals in a digital-to-analog (D/A) converter 112, and the analog signals are input to an output amplifier 114.

Amplifier 114 has a variable gain, which may be set by circuitry 132, and which is typically configured so that signal amplitudes output from the amplifier have similar values to those input to amplifier 106. In other words, while amplifier 106 is typically configured so that its output signals are larger than its input signals, the converse is true for amplifier 114, wherein its output signals are smaller than its input signals.

In a feedback generation step 160, circuitry 132 selects from the six outputs of amplifier 114 corresponding to the thermocouple signals the analog output corresponding to the maximum analog signal, derived from DIGITAL MAX TC, input to the amplifier. The selected analog output, herein termed ANALOG MAX TC, is fed back to multiplexer 102, as the feedback signal input to the multiplexer. The selection and feeding back operation is illustrated schematically in FIG. 3 by a dashed block 116 and a feedback line 118. The feedback signal input to the multiplexer is incorporated into a subsequent grouping of seven analog signals selected by the multiplexer.

While performing step 160, the control circuitry, in a comparison step 162, compares the values of DIGITAL MAX TC and DIGITAL FB as determined in step 156. If the values are different, in a gain adjustment step 164 the circuitry alters the gain of output amplifier 114 to reduce the difference in the values. If DIGITAL MAX TC>DIGITAL FB the circuitry reduces the gain; if DIGITAL MAX TC<DIGITAL FB the circuitry increases the gain. Typically, steps 162 and 164 are performed iteratively. The gain adjustment is illustrated schematically in FIG. 3 by a gain line 120.

If in comparison step 162 the values of DIGITAL MAX TC and DIGITAL FB are the same, then in a final step 166 the gain of the output amplifier is left unchanged, and the amplifier outputs its six analog signals.

In some embodiments elements of circuit 100 after multiplexer 102, comprising at least some of filter 104, amplifier 106, A/D 108, D/A 112, and amplifier 114, may be implemented as an amplification circuit 136. It will be understood that, because of the signal amplification performed by amplifier 106, and the signal "de-amplification" performed by amplifier 114, amplification circuit 136 has an overall gain approximately equal to unity.

Figure 5:
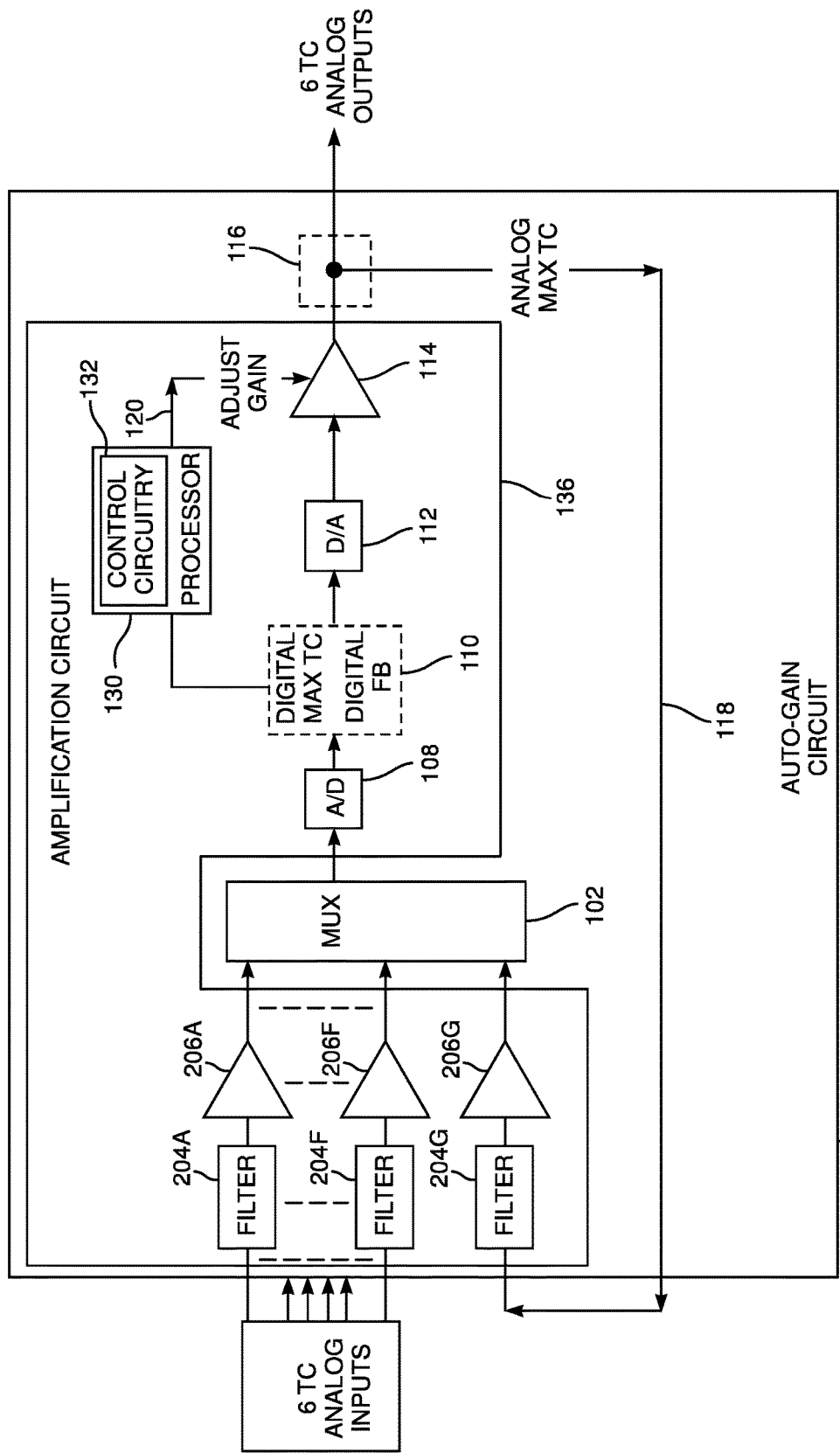
FIG. 5 is a schematic block diagram of an auto-gain circuit used for receiving signals from thermocouples, according to an alternative embodiment of the present invention.

FIG. 5 is a schematic block diagram of an auto-gain circuit 200 used for receiving the signals from thermocouples 78, according to an alternative embodiment of the present invention. Apart from the differences described below, the operation of circuit 200 is generally similar to that of circuit 100 (FIG. 3), and elements indicated by the same reference numerals in both circuits 100 and 200 are generally similar in construction and in operation.

In circuit 200, in contrast to circuit 100, each thermocouple signal is input to a filter and an amplifier, and the outputs of the amplifiers are input to multiplexer 102. Thus for the six thermocouple signals assumed herein, there are six filters followed by six amplifiers. In addition, the feedback signal (illustrated by block 116 and feedback line 118) is fed through a filter and an amplifier before the latter's output is provided to the multiplexer. Each of the filters is generally similar to filter 104, and each of the amplifiers is generally similar to amplifier 106. For simplicity, in circuit 200 only a filter 204A followed by an amplifier 206A, and a filter 204F followed by an amplifier 206F, corresponding to two of the six thermocouple inputs, are illustrated. As is also illustrated, a filter 204G, followed by an amplifier 206G, receives the feedback signal, and the amplifier output is fed to multiplexer 102.

Circuit 200 operates generally as circuit 100, and generally as is described above with respect to the flowchart of FIG. 4. Those having ordinary skill in the art will be able to adapt the description of the flowchart of FIG. 4, mutatis mutandis, to account for the differences between the two circuits.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

What is claimed is:

1. An apparatus comprising:
   a catheter having a distal section with multiple thermocouples configured to generate first multiple input signals, respectively;
   a temperature module; and
   a circuit comprising:
      a multiplexer configured to receive in parallel the first multiple input signals and a first feedback signal, and to cycle through and output serially the first multiple input signals and the first feedback signal;
      an output amplifier with a variable gain; and
      a control circuitry having a processor configured to:
         select a first selected input signal from the first multiple input signals based on a predetermined characteristic;
         perform a comparison of the first selected input signal and the first feedback signal;
         adjust the variable gain of the output amplifier in response to the comparison;
         send the first selected input signal through the adjusted output amplifier and back to the multiplexer as a second feedback signal; and
         send the first multiple input signals through the adjusted output amplifier to the temperature module.

2. The apparatus of claim 1, wherein the circuit further comprises:
   a filter configured to receive the first multiple input signals and the first feedback signal from the multiplexer; and
   an input amplifier to receive the first multiple input signals and the first feedback signal from the filter.

3. The apparatus of claim 2, wherein the input amplifier has a preset gain.

4. The apparatus of claim 3, wherein the preset gain of the input amplifier amplifies, and the variable gain of the output amplifier deamplifies.

5. The apparatus of claim 4, wherein an overall gain between the input amplifier and the output amplifier is approximately equal to unity.

6. The apparatus of claim 2, wherein the circuit further comprises an analog-to-digital converter that is configured to receive the first multiple input signals and the first feedback signal from the input amplifier, and the control circuitry is configured to receive the first multiple input signals and the first feedback signal from the analog-to-digital converter.

7. The apparatus of claim 6, wherein the circuit further comprises a digital-to-analog converter that is configured to receive the first selected input signal from the control circuitry, and the output amplifier is configured to receive the first selected input signal from the digital-to-analog converter.

8. The apparatus of claim 6, wherein the circuit further comprises a digital-to-analog converter that is configured to receive the first multiple input signals from the control circuitry, and the output amplifier is configured to receive the first multiple input signals from the digital-to-analog converter.

9. The apparatus of claim 1, wherein the predetermined characteristic includes one of the group consisting of a maximum amplitude, a minimum amplitude and a mean amplitude.

10. The apparatus of claim 1, wherein the control circuitry is configured to record the predetermined characteristic of the first feedback signal.

11. The apparatus of claim 1, wherein:
the thermocouples are configured to generate second multiple input signals subsequent to the first multiple input signals;
the multiplexer is configured to receive in parallel the second multiple input signals and the second feedback signal, and to cycle through and output serially the second multiple input signals and the second feedback signal; and
the processor is configured to:
select a second selected input signal from the second multiple input signals based on the predetermined characteristic;
perform a second comparison of the second selected input signal and the second feedback signal;
adjust the variable gain of the output amplifier depending on the second comparison;
send the second selected signal through the adjusted output amplifier and back to the multiplexer as a third feedback signal; and
send the second multiple input signals through the adjusted output amplifier to the temperature module.

12. A method, comprising:
positioning a distal section having multiple thermocouples in contact with patient tissue to generate first multiple input signals, respectively;
configuring a multiplexer to receive in parallel the first multiple input signals and a first feedback signal, and to cycle through and output the first multiple input signals and the first feedback signal;
configuring an output amplifier with a variable gain; and
configuring a control circuitry having a processor to:
select a first selected input signal from the first multiple input signals based on a predetermined characteristic;
perform a comparison of the first selected input signal and the first feedback signal;
adjust the variable gain of the output amplifier in response to the comparison;
send the first selected signal through the adjusted output amplifier and back to the multiplexer as a second feedback signal; and
send the first multiple input signals through the adjusted output amplifier to a temperature module.

13. The method of claim 12, further comprising:
configuring a filter to receive the first multiple input signals and the first feedback signal from the multiplexer; and
configuring an input amplifier to receive the first multiple input signals and the first feedback signal from the filter.

14. The method of claim 13, further comprising configuring the input amplifier with a preset gain.

15. The method of claim 13, further comprising:
configuring the input amplifier to amplify; and
configuring the output amplifier to deamplify.

16. The method of claim 13, further comprising configuring the input amplifier and the output amplifier wherein an overall gain is approximately equal to unity.

17. The method of claim 13, further comprising:
configuring an analog-to-digital converter to receive the first multiple input signals and the first feedback signal from the input amplifier, and
configuring the control circuitry to receive the first multiple input signals and the first feedback signal from the analog-to-digital converter.

18. The method of claim 17, further comprising:
configuring a digital-to-analog converter to receive the first multiple input signals from the control circuitry; and
configuring the output amplifier to receive the first multiple input signals from the digital-to-analog converter.

19. The method of claim 12, wherein the predetermined characteristic includes one of the group consisting of a maximum amplitude, a minimum amplitude and a mean amplitude.

20. The method of claim 12, further comprising:
configuring the thermocouples to generate second multiple input signals subsequent to the first multiple input signals;
configuring the multiplexer to receive in parallel the second multiple input signals and the second feedback signal, and to cycle through and output serially the second multiple input signals and the second feedback signal; and
configuring the processor to:
select a second selected input signal from the second multiple input signals based on the predetermined characteristic;
perform a second comparison of the second selected input signal and the second feedback signal;
adjust the variable gain of the output amplifier depending on the second comparison;
send the second selected input signal through the adjusted output amplifier and back to the multiplexer as a third feedback signal; and
send the second multiple input signals through the adjusted output amplifier to the temperature module.

* * * * *